(12) United States Patent
Black et al.

(10) Patent No.: US 7,422,749 B2
(45) Date of Patent: Sep. 9, 2008

(54) COMPOUNDS

(75) Inventors: Michael T. Black, Chester Spring, PA (US); Martin K. Burnham, Barto, PA (US); Jason C. Fedon, Strafford, PA (US); John E. Hodgson, Malvern, PA (US); David J. Knowles, Boroughbridge (GB); Michael A. Lonetto, Collegeville, PA (US); Richard O. Nicholas, Collegeville, PA (US); Leslie M. Palmer, Audobon, PA (US); Julie M. Pratt, Verona (IT); Raymond W. Reichard, Quakertown, PA (US); Martin Rosenberg, Royersford, PA (US); Christopher M. Traini, Guilford, PA (US); Judith Ward, Durking Surrey (GB); Richard L. Warren, Blue Bell, PA (US)

(73) Assignee: Affinium Pharmaceuticals, Inc. (CA)

( * ) Notice: Subject to any disclaimer, the term of this patent is extended or adjusted under 35 U.S.C. 154(b) by 58 days.

(21) Appl. No.: 11/698,250

(22) Filed: Jan. 25, 2007

(65) Prior Publication Data

US 2008/0076709 A1 Mar. 27, 2008

Related U.S. Application Data

(60) Division of application No. 11/166,905, filed on Jun. 23, 2005, now Pat. No. 7,176,299, which is a continuation of application No. 10/824,131, filed on Apr. 14, 2004, now abandoned, which is a continuation of application No. 09/376,633, filed on Aug. 18, 1999, now abandoned, which is a division of application No. 08/978,456, filed on Nov. 25, 1997, now Pat. No. 6,010,881, which is a continuation-in-part of application No. PCT/US97/02318, filed on Feb. 19, 1997.

(60) Provisional application No. 60/011,888, filed on Feb. 20, 1996.

(51) Int. Cl.
*A61K 39/00* (2006.01)
*C07K 1/00* (2006.01)
(52) U.S. Cl. .................... 424/185.1; 530/350
(58) Field of Classification Search .............. 424/185.1; 530/350
See application file for complete search history.

(56) References Cited

U.S. PATENT DOCUMENTS

| | | | |
|---|---|---|---|
| 5,302,527 A | 4/1994 | Birkett et al. | |
| 5,539,132 A | 7/1996 | Royer et al. | |
| 5,614,551 A | 3/1997 | Dick et al. | |
| 5,759,837 A | 6/1998 | Kuhajda et al. | |
| 5,965,402 A | 10/1999 | Black et al. | |
| 6,228,619 B1 | 5/2001 | Foster et al. | |
| 6,274,376 B1 | 8/2001 | Black et al. | |
| 6,380,370 B1 | 4/2002 | Douchette-Stamm et al. | |
| 6,403,337 B1 | 6/2002 | Bailey et al. | |
| 6,432,670 B1 | 8/2002 | Payne et al. | |
| 6,593,114 B1 | 7/2003 | Kunsch et al. | |
| 6,753,172 B1 | 6/2004 | Payne et al. | |
| 6,821,746 B2 | 11/2004 | DeWolf, Jr. et al. | |
| 6,951,729 B1 | 10/2005 | Dewolf, Jr. et al. | |
| 6,995,254 B1 | 2/2006 | Payne et al. | |
| 7,033,795 B2 | 4/2006 | DeWolf, Jr. et al. | |
| 7,048,926 B2 | 5/2006 | Brandt et al. | |
| 2002/0076766 A1 | 6/2002 | Black et al. | |
| 2004/0053814 A1 | 3/2004 | Brandt et al. | |
| 2005/0032161 A1 | 2/2005 | Black et al. | |
| 2006/0083752 A1 | 4/2006 | Black et al. | |

FOREIGN PATENT DOCUMENTS

| | | |
|---|---|---|
| DE | DT 26 20 777 | 12/1977 |
| EP | 0 78 6519 A2 | 7/1997 |
| EP | 0 826 774 A2 | 4/1998 |
| JP | 10-174590 | 6/1998 |
| WO | WO-97/30070 | 8/1997 |
| WO | WO-97/30149 | 8/1997 |
| WO | WO-00/70017 | 11/2000 |
| WO | WO-01/30988 | 5/2001 |
| WO | WO-01/48248 | 7/2001 |
| WO | WO-02/31128 | 4/2002 |

OTHER PUBLICATIONS

Bergler et al., "Protein EnvM is the NADH-dependent Enoyl-ACP Reductase (FabI) of *Escherichia coli*", *The Journal of Biological Chemistry*, vol. 269, No. 8, pp. 5493-5496 (1994).

(Continued)

*Primary Examiner*—Mark Navarro
(74) *Attorney, Agent, or Firm*—Goodwin Procter LLP

(57) ABSTRACT

This invention relates to newly identified Staphylococcal polynucleotides, polypeptides encoded by such polynucleotides, the uses of such polynucleotides and polypeptides, as well as the production of such polynucleotides and polypeptides and recombinant host cells transformed with the polynucleotides. This invention also relates to inhibiting the biosynthesis or action of such polynucleotides or polypeptides and to the use of such inhibitors in therapy.

6 Claims, No Drawings

OTHER PUBLICATIONS

Bergler et al., "Sequences of the *envM* gene and of two mutated alleles in *Escherichia coli*", Journal of General Microbiology (1992), 138, pp. 2093-2100.

Broadwater et al., "Spinach Holo-Acyl Carrier Protein: Overproduction and Phosphopantetheinylation in *Escherichia coli* BL21 (DE3), in Vitro Acylation, and Enzymatic Desaturation of Histidine-Tagged Isoform I[1]", Protein Expression and Purification 15, 314-326 (1999).

Edwards, et al., "Cloning of the fabF gene in an expression vector and in vitro characterization of recombinant *fabF* and *fabB* encoded enzymes from *Escherichia coli*", FEBS Letters, 402:62-66 (1997).

Grassberger et al., "Preparation and Antibacterial Activates of New 1,2,3-Diazaborine Derivatives and Analogues", Journal of Medicinal Chemistry, 1984, vol. 24, No. 8, pp. 947-953.

Gronowitz et al., "Antibacterial borazaro derivatives", Acta. Pharm. Suecica 8, pp. 377-390 (1971).

Heath et al., "Enoyl-Acyl Carrier Protein Reductase (*fabl*) Plays a Determinant Role in Completing Cycles of Fatty Acid Elongation in *Escherichia coli*", The Journal of Biological Chemistry, vol. 270, No. 44, pp. 26538-26542 (1995).

Heath et al., "Regulation of Fatty Acid Elongation and Initiation by Acyl-Acyl Carrier Protein in *Escherichia coli*", The Journal of Biological Chemistry, vol. 271, No. 4, pp. 1833-1836 (1996).

Lam et al., "Effect of diazaborine derivative (Sa 84.474) on the virulence of *Escherichia coli*", Journal of Antimicrobial Chemotherapy (1987) 20, pp. 37-45.

Lambalot, et al., "Cloning, Over production, and Characterization of the *Escherichia coli* Holo-acyl Carrier Protein Synthase", The Journal of Biological Chemistry, vol. 270, No. 42, pp. 24658-24661 (1995).

Rock et al., "Preparative Enzymatic Synthesis and Hydrophobic Chromotography of Acyl-Acyl Carrier Protein", The Journal of Biological Chemistry, 254 (15):7123-7128 (1979).

Rock et al., "Acyl Carrier Protein from *Escherichia coli*", Methods in Enzymology, 71:341-351 (1981).

Roujeinkova et al., "Inhibitor Binding Studies on Enoyl Reductase Reveal Conformational Changes Related to Substrate Recognition", The Journal of Biological Chemistry, 274(43): 30811-30817 (1999).

Turnowsky et al., "envM genes of *Salmonella typhimurium* and *Escerichia coli*", Journal of Bacteriology, Dec. 1989 pp. 6555-6565.

Ward et al., "Kinetic and Structureal Characteristics of the Inhibition of Enoyl (Acyl Carrier Protein) Reductase by Triclosan", Biochemistry, 38:12514-12525 (1999).

SEQUENCE LISTING

<160> NUMBER OF SEQ ID NOS: 2

<210> SEQ ID NO 1
<211> LENGTH: 194
<212> TYPE: PRT
<213> ORGANISM: Staphylococcus aureus
<220> FEATURE:
<221> NAME/KEY: MOD_RES
<222> LOCATION: (159)
<223> OTHER INFORMATION: Variable amino acid
<220> FEATURE:
<221> NAME/KEY: MOD_RES
<222> LOCATION: (178)
<223> OTHER INFORMATION: Variable amino acid
<220> FEATURE:
<221> NAME/KEY: MOD_RES
<222> LOCATION: (184)
<223> OTHER INFORMATION: Variable amino acid

<400> SEQUENCE: 1

```
Met Glu Asp Leu Arg Gly Arg Phe Ser Glu Thr Ser Arg Glu Gly Phe
 1               5                  10                  15

Leu Leu Ala Gln Asp Ile Ser Ser Tyr Ser Leu Thr Ile Val Ala His
            20                  25                  30

Glu Ala Lys Lys Leu Met Pro Glu Gly Gly Ser Ile Val Ala Thr Thr
        35                  40                  45

Tyr Leu Gly Gly Glu Phe Ala Val Gln Asn Tyr Asn Val Met Gly Val
    50                  55                  60

Ala Lys Ala Ser Leu Glu Ala Asn Val Lys Tyr Leu Ala Leu Asp Leu
65                  70                  75                  80
```

```
Gly Pro Asp Asn Ile Arg Val Asn Ala Ile Ser Ala Gly Pro Ile Arg
                 85                  90                  95

Thr Leu Ser Ala Lys Gly Val Gly Phe Asn Thr Ile Leu Lys Glu
            100                 105                 110

Ile Glu Glu Arg Ala Pro Leu Lys Arg Asn Val Asp Gln Val Glu Val
        115                 120                 125

Gly Lys Thr Ala Ala Tyr Leu Leu Ser Asp Leu Ser Ser Gly Val Thr
    130                 135                 140

Gly Glu Asn Ile His Val Asp Ser Gly Phe His Ala Ile Asn Xaa Ile
145                 150                 155                 160

Ile Gln Gln Leu Gly Phe Thr Val Tyr His Ile Leu Trp Ser Lys Ser
                165                 170                 175

Phe Xaa Gly Phe Ile Asn Asn Xaa Ala Asp Gly Lys Leu Leu Asp Ile
        180                 185                 190

Ser Thr

<210> SEQ ID NO 2
<211> LENGTH: 1167
<212> TYPE: DNA
<213> ORGANISM: Staphylococcus aureus
<220> FEATURE:
<221> NAME/KEY: modified_base
<222> LOCATION: (1051)
<223> OTHER INFORMATION: a, c, g, t, unknown or other
<220> FEATURE:
<221> NAME/KEY: modified_base
<222> LOCATION: (1107)
<223> OTHER INFORMATION: a, c, g, t, unknown or other
<220> FEATURE:
<221> NAME/KEY: modified_base
<222> LOCATION: (1126)
<223> OTHER INFORMATION: a, c, g, t, unknown or other

<400> SEQUENCE: 2
atatgatatt aaaatgcagg aacgtattta gtacgaacgt aaaattaatg atttaaaatg      60
ctagtatgta tatgattttg ataaataaat gcttttttaac gtaaatcaag tttgatacag    120
aaaggactaa atcaaaacat ttattcgttg taataacgtt taaataactt tattaaaaag    180
tcataatagt gttaaaatgt attgacgaat aaaaagttag ttaaaactgg gattagatat    240
tctatccgtt aaattaatta ttataaggag ttatcttaac atgttaaatc ttgaaaacaa    300
aacatatgtc atcatgggaa tcgctaataa gcgtagtatt gcttttggtg tcgctaaagt    360
tttaagatca attaggtgct aaattagtat ttacttaccg taaagaacgt agccgtaaag    420
agcttgaaaa attattagaa caattaaatc aaccagaagc gcacttatat caaattgatg    480
ttcaaagcga tgaagaggtt attaatggtt ttgagcaaat tggtaaagat gttggcaata    540
ttgatggtgt atatcattca atcgcatttg ctaatatgga agacttacgc ggacgctttt    600
ctgaaacttc acgtgaaggc ttcttgttag ctcaagacat tagttcttac tcattaacaa    660
ttgtggctca tgaagctaaa aaattaatgc cagaaggtgg tagcattgtt gcaacaacat    720
atttaggtgg cgaattcgca gttcaaaatt taatgtgat gggtgttgct aaagcgagct    780
tagaagcaaa tgttaaatat ttagcattag acttaggtcc tgataatatt cgcgttaatg    840
caatttcagc tggtccaatc cgtacattaa gtgcaaaagg tgtgggtggt ttcaatacaa    900
ttcttaaaga aatcgaagag cgtgcacctt taaaacgtaa cgttgatcaa gtagaagtag    960
gtaaaacagc ggcttactta ttaagtgact atcaagtgg cgttacaggt gaaaatattc   1020
atgtagatag cggattccac gcaattaata ntatcattca acagcttggg ttcaccgttt   1080
```

-continued

```
atcatatatt gtggagcaaa agctttntgg gttttattaa taatcnggct gatggaaaat    1140
tattggatat ttcaacctga cttgatt                                        1167
```

COMPOUNDS

RELATED APPLICATION INFORMATION

This application is a divisional of U.S. Ser. No. 11/166,905, filed Jun. 23, 2005, now U.S. Pat. No. 7,176,299 which is a continuation of U.S. Ser. No. 10/824,131 filed Apr. 14, 2004, abandoned, which is a continuation of U.S. Ser. No. 09/376,633 filed Aug. 18, 1999, abandoned, which is a divisional of Ser. No. 08/978,456 filed Nov. 25, 1997, now U.S. Pat. No. 6,010,881, which is a continuation-in-part of PCT/US97/02318 filed Feb. 19, 1997, which claims priority to provisional application 60/011,888 filed Feb. 20, 1996, all of which are hereby incorporated by reference.

FIELD OF THE INVENTION

This invention relates to newly identified polynucleotides, particularly Staphylococcal polynucleotides, polypeptides encoded by such polynucleotides, the uses of such polynucleotides and polypeptides, as well as the production of such polynucleotides and polypeptides and recombinant host cells transformed with the polynucleotides. This invention also relates to activating or inhibiting the biosynthesis or action of such polynucleotides or polypeptides and to the use of such activators or inhibitors in therapy.

BACKGROUND OF THE INVENTION

The Staphylococci make up a medically important genera of microbes. They are known to produce two types of disease, invasive and toxigenic. Invasive infections are characterized generally by abscess formation effecting both skin surfaces and deep tissue. *Staphylococcus aureus* (*S. aureus*) is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

While certain Staphylococcal proteins associated with pathogenicity have been identified, e.g., coagulase, hemolysins, leucocidins and exo and enterotoxins, very little is known concerning the temporal expression of such genes during infection and disease progression in a mammalian host. Discovering the sets of genes the bacterium is likely to be expressing at the different stages of infection, particularly when an infection is established, provides critical information for the screening and characterization of novel antibacterials which can interrupt pathogenesis. In addition to providing a fuller understanding of known proteins, such an approach will identify previously unrecognized targets.

BRIEF DESCRIPTION OF THE INVENTION

This invention provides novel protein from *Staphylococcus aureus* WCUH29, characterized in that it comprises the amino acid sequence given herein or a fragment, analogue or derivative thereof. Also provided by the invention is an isolated polypeptide comprising an acid sequence selected from the group consisting of SEQ ID NO: 1.

Further provided by the invention is an isolated nucleic acid (herein also "polynucleotide") encoding one of the amino acid sequences of SEQ ID NO: 1, or an isolated polynucleotide sequence selected from the group consisting of SEQ ID NO:2 or any polynucleotide sequences capable of hybridizing therewith under stringent conditions.

In accordance with another aspect of the present invention, there are provided polynucleotides (DNA or RNA) which encode such polypeptides.

In particular the invention provides polynucleotides having the DNA sequences given herein.

The invention also relates to novel oligonucleotides derived from the sequences given herein which can act as PCR primers in the process herein described to determine whether or not the gene identified herein, particularly a *Staphylococcus aureus* gene, in whole or in part is expressed in infected tissue. It is recognized that such sequences will also have utility in diagnosis of the stage of infection and type of infection the pathogen has attained. The proteins so identified are also useful as targets in screens designed to identify antimicrobial compounds.

DETAILED DESCRIPTION OF THE INVENTION

Each of the polynucleotide sequences provided herein, particularly the DNA sequences, may be used in the discovery and development of antibacterial compounds. Because each of the sequences contains an open reading frame (ORF) or putative gene with an appropriate initiation and termination codons, the encoded protein upon expression can be used as a target for the screening of antimicrobial compounds, such as drugs. Additionally, the DNA sequences encoding the amino terminal regions of the encoded protein can be used to construct antisense or ribozyme sequences to control the expression of the coding sequence of interest. Furthermore, many of the sequences disclosed herein also provide regions upstream and downstream from the encoding sequence. These sequences are useful as a source of regulatory elements for the control of bacterial gene expression. Such sequences are conveniently isolated by restriction enzyme action or synthesized chemically and introduced, for example, into promoter identification strains. These strains contain a reporter structural gene sequence located downstream from a restriction site such that if an active promoter is inserted, the reporter gene will be expressed.

Although each of the sequences may be employed as described above, this invention also provides several means for identifying particularly useful target genes. The first of these approaches entails searching appropriate databases for sequence matches in related organisms. Thus, if a homologue exists, the Staphylococcal-like form of this gene would likely play an analogous role. For example, a Staphylococcal protein identified as homologous to a cell surface protein in another organism would be useful as a vaccine candidate. To the extent such homologies have been identified for the sequences disclosed herein they are reported along with the coding sequence.

Recently techniques have become available to evaluate temporal gene expression in bacteria, particularly as it applies to viability under laboratory and infection conditions. A number of methods can be used to identify genes which are essential to survival per se, or essential to the establishment/maintenance of an infection. Identification of an ORF unknown by one of these methods yields additional information about its function and permits the selection of such an ORF for further development as a screening target. Briefly, these approaches include:

1) Signature Tagged Mutagenesis (STM)

This technique is described by Hensel et al., *Science* 269: 400-403 (1995), the contents of which is incorporated by reference for background purposes. Signature tagged mutagenesis identifies genes necessary for the establishment/ maintenance of infection in a given infection model.

The basis of the technique is the random mutagenesis of target organism by various means (e.g., transposons) such that unique DNA sequence tags are inserted in close proximity to the site of mutation. The tags from a mixed population of bacterial mutants and bacteria recovered from an infected hosts are detected by amplification, radiolabeling and hybridization analysis. Mutants attenuated in virulence are revealed by absence of the tag from the pool of bacteria recovered from infected hosts.

2) In Vivo Expression Technology (IVET).

This technique is described by Camilli et al., *Proc. Nat'l Acad. Sci. USA.* 91:2634-2638 (1994), the contents of which is incorporated by reference for background purposes. IVET identifies genes up-regulated during infection when compared to laboratory cultivation, implying an important role in infection. ORF identified by this technique are implied to have a significant role in infection establishment/maintenance. In this technique random chromosomal fragments of target organism are cloned upstream of a promoter-less recombinase gene in a plasmid vector. This construct is introduced into the target organism which carries an antibiotic resistance gene flanked by resolvase sites. Growth in the presence of the antibiotic removes from the population those fragments cloned into the plasmid vector capable of supporting transcription of the recombinase gene and therefore have caused loss of antibiotic resistance. The resistant pool is introduced into a host and at various times after infection bacteria may be recovered and assessed for the presence of antibiotic resistance. The chromosomal fragment carried by each antibiotic sensitive bacterium should carry a promoter or portion of a gene normally upregulated during infection. Sequencing upstream of the recombinase gene allows identification of the up regulated gene.

3) Differential Display.

This technique is described by Chuang et al, *J. Bacteriol.* 175:2026-2036 (1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to ORF 'unknowns'.

4) Generation of Conditional Lethal Mutants by Transposon Mutagenesis.

This technique, described by de Lorenzo, V. et al., *Gene* 123:17-24 (1993); Neuwald, A. F. et al., *Gene* 125: 69-73 (1993); and Takiff, H. E. et al., *J. Bacteriol.* 174:1544-1553 (1992), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of Conditional Lethal Mutants by Chemical Mutagenesis.

This technique is described by Beckwith, *J. Methods in Enzymology* 204: 3-18 (1991), the contents of which are incorporated herein by reference for background purposes. In this technique random chemical mutagenesis of target organism, growth at temperature other than physiological temperature (permissive temperature) and subsequent replica plating and growth at different temperature (e.g. 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with unknown ORF.

Each of these techniques may have advantages or disadvantage depending on the particular application. The skilled artisan would choose the approach that is the most relevant with the particular end use in mind. For example, some genes might be recognized as essential for infection but in reality are only necessary for the initiation of infection and so their products would represent relatively unattractive targets for antibacterials developed to cure established and chronic infections.

In yet another variation, a suitably labelled oligonucleotide probe which anneals specifically to the bacterial ribosomal RNA in Northern blots of bacterial RNA preparations from infected tissue is employed. Using the more abundant ribosomal RNA as a hybridization target greatly facilitates the optimization of a protocol to purify bacterial RNA of a suitable size for RT-PCR from infected tissue.

Use of the of these technologies when applied to the OREs of the present invention enables identification of bacterial proteins expressed during infection, inhibitors of which would have utility in anti-bacterial therapy.

*S. aureus* WCUH 29 has been deposited at the National Collection of Industrial and Marine Bacteria Ltd. (NCIMB), Aberdeen, Scotland under number NCIMB 40771 on 111 Sep. 1995.

The nucleotide sequences disclosed herein can be obtained by synthetic chemical techniques known in the art or can be obtained from *S. aureus* WCUH 29 by probing a DNA preparation with probes constructed from the particular sequences disclosed herein. Alternatively, oligonucleotides derived from a disclosed sequence can act as PCR primers in a process of PCR-based cloning of the sequence from a bacterial genomic source. It is recognized that such sequences will also have utility in diagnosis of the stage of infection and type of infection the pathogen has attained.

To obtain the polynucleotide encoding the protein using the DNA sequence given herein typically a library of clones of chromosomal DNA of *S. aureus* WCUH29 in *E. Coli* or some other suitable host is probed with a radiolabelled oligonucleotide, preferably a 17mer or longer, derived from the partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook, J. in MOLECULAR CLONING, A Laboratory Manual, 2nd edition, 1989, Cold Spring Harbor Laboratory (see: Screening By Hybridization 1.90 and Sequencing Denatured Double-Stranded DNA Templates 13.70).

A polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the polypeptide may be identical to the coding sequence shown or may be a different coding sequence which coding sequence, as a result of the redundancy or degeneracy of the genetic code, encoding the same polypeptide.

The present invention includes variants of the hereinabove described polynucleotides which encode fragments, analogues and derivatives of the polypeptide characterized by the deduced amino acid sequence given herein. The variant of the polynucleotide may be a naturally occurring allelic variant of the polynucleotide or a nonnaturally occurring variant of the polynucleotide. In addition to the standard A, G, C, T/U representations for nucleic acid bases, the term "N" is also used in certain polynucleotides of the invention. "N" means that any of the four DNA or RNA bases may appear at such a designated position in the DNA or RNA sequence, except that in preferred embodiments N cannot be a base that when taken in combination with adjacent nucleotide positions, when read in the correct reading frame, would have the effect of generating a premature termination codon in such reading frame. Thus, the present invention includes polynucleotides encoding the same polypeptide characterized by the deduced amino acid sequence given herein as well as variants of such polynucleotides which variants encode for a fragment, derivative or analogue of the polypeptide. Such nucleotide variants include deletion variants, substitution variants and addition or insertion variants. The polynucleotide may have a coding sequence which is a naturally occurring allelic variant of the coding sequence characterized by the DNA sequence disclosed herein.

As known in the art, an allelic variant is an alternate form of a polynucleotide sequence which may have a substitution, deletion or addition of one or more nucleotides, which does not substantially alter the function of the encoded polypeptide. The polynucleotide which encodes for the mature polypeptide, may include only the coding sequence for the mature polypeptide or the coding sequence for the mature polypeptide and additional coding sequence such as a leader or secretory sequence or a proprotein sequence.

Thus, the term "polynucleotide encoding a polypeptide" encompasses a polynucleotide which includes only coding sequence for the polypeptide as well as a polynucleotide which includes additional coding and/or non-coding sequence.

The present invention therefore includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence). Further, the amino acid sequences provided herein show a methionine residue at the NH2-terminus. It is appreciated, however, that during post-translational modification of the peptide, this residue may be deleted. Accordingly, this invention contemplates the use of both the methionine-containing and the methionineless amino terminal variants of each protein disclosed herein.

The polynucleotides of the present invention may also have the coding sequence fused in frame to a marker sequence at either the 5' or 3' terminus of the gene which allows for purification of the polypeptide of the present invention. The marker sequence may be a hexa-histidine tag supplied by the pQE series of vectors (supplied commercially by Quiagen Inc.) to provide for purification of the polypeptide fused to the marker in the case of a bacterial host.

The present invention further relates to polynucleotides which hybridize to the hereinabove-described sequences if there is at least 50% or 60% and preferably at least 70%, 80% or 90% identity between the sequences. The present invention particularly relates to Staphylococcal polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the polypeptide characterized by the deduced amino acid sequence given herein.

The deposit referred to herein will be maintained under the terms of the Budapest Treaty on the International Recognition of the Deposit of Micro-organisms for purposes of patent Procedure. These deposits are provided merely as convenience to those of skill in the art and are not an admission that a deposit is required under 35 U.S.C. 112. The sequence of the polynucleotides contained in the deposited material, as well as the amino acid sequence of the polypeptides encoded thereby, are incorporated herein by reference and are controlling in the event of any conflict with any description of sequences herein. A license may be required to make, use or sell the deposited material, and no such license is hereby granted.

The terms "fragment," "derivative" and "analogue" when referring to the polypeptide characterized by the deduced amino acid sequence herein, means a polypeptide which retains essentially the same biological function or activity as such polypeptide. Thus, an analogue includes a proprotein which can be activated by cleavage of the proprotein portion to produce an active mature polypeptide. The polypeptide of the present invention may be a recombinant polypeptide, a natural polypeptide or a synthetic polypeptide, preferably a recombinant polypeptide.

The fragment, derivative or analogue of the polypeptide characterized by the deduced amino acid sequence herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the polypeptide or a proprotein sequence. Such fragments, derivatives and analogues are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

In accordance with yet a further aspect of the present invention, there is therefore provided a process for producing the polypeptide of the invention by recombinant techniques by expressing a polynucleotide encoding said polypeptide in a host and recovering the expressed product. Alternatively, the polypeptides of the invention can be synthetically produced by conventional peptide synthesizers. Host cells are genetically engineered (transduced or transformed or transfected) with the vectors of this invention which may be, for example, a cloning vector or an expression vector. The vector may be, for example, in the form of a plasmid, a cosmid, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan. Suitable expression vectors include chromosomal, nonchromosomal and synthetic DNA sequences, e.g., bacterial plasmids; phage DNA; baculovirus; yeast plasmids; vectors derived from combinations of plasmids and phage DNA. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. The DNA sequence in the expression vector is operatively linked to an appropriate expression control sequence(s) (promoter) to direct mRNA synthesis. As representative examples of such promoters, there may be mentioned: LTR or SV40 promoter, the *E. Coli*.lac or trp, the phage lambda PL promoter and other promoters known to control expression of genes in eukaryotic or prokaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The polypeptides of the present invention can be expressed using, for example, the *E. Coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397. Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

Generally, recombinant expression vectors will include origins of replication and selectable markers permitting transformation of the host cell, e.g., the ampicillin resistance gene of *E. coli* and *S. cerevisiae* TRP 1 gene, and a promoter derived from a highly expressed gene to direct transcription of a downstream structural sequence. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

The vector containing the appropriate DNA sequence as hereinabove described, as well as an appropriate promoter or control sequence, may be employed to transform an appropriate host to permit the host to express the protein. More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pET-3 vectors (Stratagene), pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRITS (Pharmacia). Eukaryotic:pBlueBacIII (Invitrogen), pWLNEO, pSV2CAT, pOG44, pXTI, pSG (Stratagene) pSVK3, pBPV, pMSG, pSVL (Pharmacia). However, any other plasmid or vector may be used as long as they are replicable and viable in the host.

Examples of recombinant DNA vectors for cloning and host cells which they can transform include the bacteriophage 1 (*E. coli*), pBR322 (*E. coli*), pACYC177 (*E. coli*), pKT230 (gram-negative bacteria), pGV1106 (gram-negative bacteria), pLAFR 1 (gramnegative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (Streptomyces), YIp5 (Saccharomyces), a baculovirus insect cell system, YCpl9 (*Saccharomyces*). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

In some cases, it may be desirable to add sequences which cause the secretion of the polypeptide from the host organism, with subsequent cleavage of the secretory signal.

Polypeptides can be expressed in host cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crudeextracfretained for further purification.

Microbial cells employed in expression of proteins can be disrupted by any convenient method, including freeze-thaw cycling, sonication, mechanical disruption, or use of cell lysing agents, such methods are well known to those skilled in the art.

Depending on the expression system and host selected, the polypeptide of the present invention may be produced by growing host cells transformed by an expression vector described above under conditions whereby the polypeptide of interest is expressed. The polypeptide is then isolated from the host cells and purified. If the expression system secretes the polypeptide into growth media, the polypeptide can be purified directly from the media. If the polypeptide is not secreted, it is isolated from cell lysates or recovered from the cell membrane fraction. Where the polypeptide is localized to the cell surface, whole cells or isolated membranes can be used as an assayable source of the desired gene product. Polypeptide expressed in bacterial hosts such as *E. Coli* may require isolation from inclusion bodies and refolding. Where the mature protein has a very hydrophobic region which leads to an insoluble product of overexpression, it may be desirable to express a truncated protein in which the hydrophobic region has been deleted. The selection of the appropriate growth conditions and recovery methods are within the skill of the art.

The polypeptide can be recovered and purified from recombinant cell cultures by methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

Depending upon the host employed in a recombinant production procedure, the polypeptides of the present invention may be glycosylated or may be non-glycosylated. Polypeptides of the invention may also include an initial methionine amino acid residue.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG, GTG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature.

In accordance with yet a further aspect of the present invention, there is provided the use of a polypeptide of the invention for therapeutic or prophylactic purposes, for example, as an antibacterial agent or a vaccine.

In accordance with another aspect of the present invention, there is provided the use of a polynucleotide of the invention for therapeutic or prophylactic purposes, in particular genetic immunization.

In accordance with yet another aspect of the present invention, there are provided inhibitors to such polypeptides, useful as antibacterial agents. In particular, there are provided antibodies against such polypeptides.

Another aspect of the invention is a pharmaceutical composition comprising the above polypeptide, polynucleotide or inhibitor of the invention and a pharmaceutically acceptable carrier. In a particular aspect the invention provides the use of an inhibitor of the invention as an antibacterial agent.

The invention further relates to the manufacture of a medicament for such uses.

The polypeptide may be used as an antigen for vaccination of a host to produce specific antibodies which have antibacterial action.

The polypeptides or cells expressing them can be used as an immunogen to produce antibodies thereto. These antibodies can be, for example, polyclonal or monoclonal antibodies. The term antibodies also includes chimeric, single chain, and humanized or simianized antibodies, as well as Fab fragments, or the product of an Fab expression library. Various procedures known in the art may be used for the production of such antibodies and fragments.

Antibodies generated against the polypeptides of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Polypeptide derivatives include antigenically or immunologically equivalent derivatives which form a particular aspect of this invention.

The term 'antigenically equivalent derivative' as used herein encompasses a polypeptide or its equivalent which will be specifically recognized by certain antibodies which, when raised to the protein or polypeptide according to the present invention, interfere with the interaction between pathogen and mammalian host.

The term 'immunologically equivalent derivative' as used herein encompasses a peptide or its equivalent which when used in a suitable formulation to raise antibodies in a vertebrate, the antibodies act to interfere with the interaction between pathogen and mammalian host.

In particular derivatives which are slightly longer or slightly shorter than the native protein or polypeptide fragment of the present invention may be used. In addition, polypeptides in which one or more of the amino acid residues are modified may be used. Such peptides may, for example, be prepared by substitution, addition, or rearrangement of amino acids or by chemical modification thereof. All such substitutions and modifications are generally well known to those skilled in the art of peptide chemistry.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof maybe sufficiently antigenic to improve immunogenicity so as to obviate the use of a carrier.

For preparation of monoclonal antibodies, any technique which provides antibodies produced by continuous cell line cultures can be used. Examples include the hybridoma technique (Kohler and Milstein, *Nature*, 256:495-497 (1975)), the trioma technique, the human B-cell hybridoma technique (Kozbor et al., *Immunology Today* 4:72 (1983)), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention.

Using the procedure of Kohler and Milstein (*supra*, (1975)), antibody-containing cells from the immunized mammal are fused with myeloma cells to create hybridoma cells secreting monoclonal antibodies.

The hybridomas are screened to select a cell line with high binding affinity and favorable cross reaction with other staphylococcal species using one or more of the original polypeptide and/or the fusion protein. The selected cell line is cultured to obtain the desired Mab.

Hybridoma cell lines secreting the monoclonal antibody are another aspect of this invention.

Alternatively phage display technology could be utilized to select antibody genes with binding activities towards the polypeptide either from repertoires of PCR amplified vgenes of lymphocytes from humans screened for possessing anti-Fbp or from naive libraries (McCafferty, J. et al., *Nature* 348:552-554 (1990), and Marks, J. et al., *Biotechnology* 10:779-783 (1992)). The affinity of these antibodies can also be improved by chain shuffling (Clackson, T. et al., *Nature* 352:624-628 (1991)).

The antibody should be screened again for high affinity to the polypeptide and/or fusion protein.

As mentioned above, a fragment of the final antibody may be prepared.

The antibody may be either intact antibody of $M_r$ approx 150,000 or a derivative of it, for example a Fab fragment or a Fv fragment as described in Skerra, A and Pluckthun, A., *Science* 240:1038-1040 (1988). If two antigen binding domains are present each domain may be directed against a different epitope—termed 'bispecific' antibodies. The antibody of the invention may be prepared by conventional means for example by established monoclonal antibody technology (Kohler, G. and Milstein, C. (*supra*, (1975) or using recombinant means e.g. combinatorial libraries, for example as described in Huse, W. D. et al., *Science* 246:1275-1281 (1989).

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or *Streptomyces sp.* or a eukaryotic cell, such as a mouse C127, mouse myeloma, human HeLa, Chinese hamster ovary, filamentous or unicellular fungi or insect cell. The host may also be a transgenic animal or a transgenic plant (for example, as described in Hiatt, A. et al., *Nature* 340:76-78 (1989). Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.

Preferably the antibody or derivative thereof is modified to make it less immunogenic in the patient. For example, if the patient is human the antibody may most preferably be 'humanized'; where the complimentary determining region(s) of the hybridoma-derived antibody has been transplanted into a human monoclonal antibody, for example as described in Jones, P. et al., *Nature* 321:522-525 (1986), or Tempest et al., *Biotechnology* 9:266-273 (1991).

The modification need not be restricted to one of 'humanization'; other primate sequences (for example Newman, R. et al., *Biotechnology* 10:1455-1460 (1992)) may also be used.

The humanized monoclonal antibody, or its fragment having binding activity, form a particular aspect of this invention.

This invention provides a method of screening compounds, for example, drugs to identify those which activate or preferably interfere with the proteins selected as targets herein, which method comprises measuring the activation or interference of the activity of the protein by a test compound or drug. For example if the protein selected has a catalytic activity, after suitable purification and formulation the activity of the enzyme can be followed by its ability to convert its natural substrates. By incorporating different chemically synthesized test compounds or natural products into such an assay of enzymatic activity one is able to detect those additives which compete with the natural substrate or otherwise inhibit enzymatic activity.

The invention also relates to inhibitors identified thereby.

The use of a polynucleotide of the invention in genetic immunization will preferably employ a suitable delivery method such as direct injection of plasmid DNA into muscles (Wolff et al., *Hum. Mol. Genet.* 1:363 (1992); Manthorpe et al., *Hum. Gene Ther.* 4:419 (1963)), delivery of DNA complexed with specific protein carriers (Wu et al., *J. Biol. Chem.* 264:16985 (1989)), coprecipitation of DNA with calcium phosphate (Benvenisty & Reshef, *Proc. Nat'l Acad. Sci. USA*, 83:9551 (1986)), encapsulation of DNA in various forms of liposomes (Kaneda et al., *Science* 243:375 (1989)), particle bombardment (Tang et al., *Nature* 356:152 (1992)); Eisenbraun et al., *DNA Cell Biol.* 12:791 (1993)) and in vivo infection using cloned retroviral vectors (Seeger et al., *Proc. Nat'l. Acad. Sci. USA* 81:5849 (1984)). Suitable promoters for muscle transfection include CMV, RSV, SRa, actin, MCK, alpha globin, adenovirus and dihydrofolate reductase.

In therapy or as a prophylactic, the active agent i.e., the polypeptide, polynucleotide or inhibitor of the invention, may be administered to a patient as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to human patients, it is expected that the daily dosage level of the active agent will be from 0.01 to 10 mg/kg, typically around 1 mg/kg. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

A vaccine composition is conveniently in injectable form. Conventional adjuvants may be employed to enhance the immune response.

A suitable unit dose for vaccination is 0.5-5 ug/kg of antigen, and such dose is preferably administered 1-3 times and with an interval of 1-3 weeks.

Within the indicated dosage range, no adverse toxicologicals effects are expected with the compounds of the invention which would preclude their administration to suitable patients.

EXAMPLES

In order to facilitate understanding of the following non-limiting examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37 C are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., (1980) Nucleic Acids Res., 8:4057.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., *supra*., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Example 1

Isolation of DNA Coding for a Novel Protein from *S. Aureus* WCUH 29

The polynucleotide having the DNA sequence given herein can be obtained from a library of clones of chromosomal DNA of *S. aureus* WCUH 29 in *E. coli*. Libraries may be prepared by routine methods, for example:

Methods 1 and 2.

Total cellular DNA is isolated from *Staphylococcus aureus* strain WCUH29 (NCIMB 40771) according to standard procedures and size-fractionated by either of two methods.

Method 1.

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2.

Total cellular DNA is partially hydrolyzed with a combination of four restriction enzymes (RsaI, PalI, AluI and BshI 2351) and size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

The Determination of Expression During Infection of a Gene from *Staphylococcus Aureus* WCUH29

Necrotic fatty tissue from a four day groin infection of *Staphylococcus aureus* WCUH29 in the mouse is efficiently disrupted and processed in the presence of chaotropic agents and RNAase inhibitor to provide a mixture of animal and bacterial RNA. The optimal conditions for disruption and processing to give stable preparations and high yields of bacterial RNA are followed by the use of hybridization to a radiolabelled oligonucleotide specific to *Staphylococcus aureus* 16S RNA on Northern blots. The RNase free, DNase free, DNA and protein free preparations of RNA obtained are suitable for Reverse Transcription PCR (RT-PCR) using unique primer pairs designed from the sequence of each gene of *Staphylococcus aureus* WCUH29.

a) Isolation of Tissue Infected with *Staphylococcal aureus* WCUH29 from a Mouse Animal Model of Infection 10 ml. volumes of sterile nutrient broth (No. 2 Oxoid) are seeded with isolated, individual colonies of *Staphylococcus aureus* WCUH29 from an agar culture plate.

The cultures are incubated aerobically (static culture) at 37 degrees C for 16-20 hours. 4 week old mice (female, 18 g-22 g, strain MF1) are each infected by subcutaneous injection of 0.5 ml. of this broth culture of *Staphylococcus aureus* WCUH29 (diluted in broth to approximately 108 cfu/ml.) into the anterior, right lower quadrant (groin area). Mice should be monitored regularly during the first 24 hours after infection, then daily until termination of study. Animals with signs of systemic infection, i.e. lethargy, ruffled appearance, isolation from group, should be monitored closely and if signs progress to moribundancy, the animal should be culled immediately.

Visible external signs of lesion development will be seen 24-48 h after infection. Examination of the abdomen of the animal will show the raised outline of the abscess beneath the skin. The localized lesion should remain in the right lower quadrant, but may occasionally spread to the left lower quadrant, and superiorly to the thorax. On occasions, the abscess may rupture through the overlying skin layers. The affected animal should be culled immediately and the tissues sampled if possible. Failure to cull the animal may result in the necrotic skin tissue overlying the abscess being sloughed off, exposing the abdominal muscle wall.

Approximately 96 h after infection, animals are killed using carbon dioxide asphyxiation. To minimize delay between death and tissue processing/storage, mice should be killed individually rather than in groups. The dead animal is placed onto its back and the fur swabbed liberally with 70% alcohol. An initial incision using scissors is made through the skin of the abdominal left lower quadrant, travelling superiorly up to, then across the thorax. The incision is completed by cutting inferiorly to the abdominal lower right quadrant. Care should be taken not to penetrate the abdominal wall. Holding the skin flap with forceps, the skin is gently pulled way from the abdomen. The exposed abscess, which covers the peritoneal wall but generally does not penetrate the muscle sheet completely, is excised, taking care not to puncture the viscera.

The abscess/muscle sheet and other infected tissue, such as the necrotic pads of fatty tissue in the abdominal lower right and left quadrants may require cutting in sections, prior to flash-freezing in liquid nitrogen, thereby allowing easier storage in plastic collecting vials.

b) Isolation of *Staphylococcus Aureus* WCUH29 RNA from Infected Tissue Samples 4-6 infected tissue samples (each approx 0.5-0.7 g) in 2 ml screw-cap tubes are removed from -80 C storage into a dry ice ethanol bath In a microbiological safety cabinet the samples are disrupted individually whilst the remaining samples are kept cold in the dry ice ethanol bath. To disrupt the bacteria within the tissue samplelml of TRIzol Reagent (Gibco BRL, Life Technologies) is added followed by enough 0.1 mm zirconia/silica beads to almost fill the tube, the lid is replaced taking care not to get any beads into the screw thread so as to ensure a good seal and eliminate aerosol generation. The sample is then homogenized in a Mini-BeadBeater TypeBX4 (Biospec Products) Necrotic fatty tissue is treated for 100 seconds at 5000 rpm in order to achieve bacterial lysis. In vivo grown bacteria require longer treatment than in vitro grown *S. aureus* WCUH29 which are disrupted by a 30 second bead-beat.

After bead-beating the tubes are chilled on ice before opening in a fume-hood as heat generated during disruption may degrade the TRIzol and release cyanide. 200 microliters of chloroform is then added and the tubes shaken by hand for 15 seconds to ensure complete mixing. After 2-3 minutes at room temperature the tubes are spun down at 12,000×g, 4° C. for 15 minutes and RNA extraction is then continued according to the method given by the manufacturers of TRIzol Reagent i.e.: —The aqueous phase, approx 0.6 ml, is transferred to a sterile eppendorf tube and 0.5 ml of isopropanol is added. After 10 minutes at room temperature the samples are spun at 12,000×g, 4° C. for 10 minutes. The supernatant is removed and discarded then the RNA pellet is washed with 1 ml 75% ethanol. A brief vortex is used to mix the sample before centrifuging at 7,500×g, 4° C. for 5 minutes. The ethanol is removed and the RNA pellet dried under vacuum for no more than 5 minutes. Samples are then resuspended by repeated pipetting in 100 microliters of DEPC treated water, followed by 5-10 minutes at 55° C. Finally, after at least 1 minute on ice, 200 units of Rnasin (Promega) is added. RNA preparations are stored at −80° C. for up to one month. For longer term storage the RNA precipitate can be stored at the wash stage of the protocol in 75% ethanol for at least one year at −20° C.

Quality of the RNA isolated is assessed by running samples on 1% agarose gels. 1×TBE gels stained with ethidium bromide are used to visualize total RNA yields. To demonstrate the isolation of bacterial RNA from the infected tissue 1×MOPS, 2.2M formaldehyde gels are run and vacuum blotted to Hybond-N (Amersham). The blot is then hybridized with a $^{32}$P labelled oligonucleotide probe specific to 16s rRNA of *S. aureus* (K. Greisen, et al., *J. Clin. Microbiol.* 32 335-351 (1994)). An oligonucleotide of the sequence: 5'-gctcctaaaaggttactccaccggc-3' [SEQ ID NO: 1166] is used as a probe. The size of the hybridizing band is compared to that of control RNA isolated from in vitro grown *S. aureus* WCUH29. Correct sized bacterial 16s rRNA bands can be detected in total RNA samples which show extensive degradation of the mammalian RNA when visualized on TBE gels.

c) The Removal of DNA from *Staphylococcus Aureus* WCUH29 Derived RNA

DNA was removed from 73 microliter samples of RNA by a 15 minute treatment on ice with 3 units of DNaseI, amplification grade (Gibco BRL, Life Technologies) in the buffer supplied with the addition of 200 units of Rnasin (Promega) in a final volume of 90 microliters. The DNase was inactivated and removed by treatment with TRIzol LS Reagent (Gibco BRL, Life Technologies) according to the manufacturers protocol. DNase treated RNA was resuspended in 73 microliters of DEPC treated water with the addition of Rnasin as described in Method 1.

d) The Preparation of cDNA from RNA Samples Derived from Infected Tissue 10 microliter samples of DNase treated RNA are reverse transcribed using a SuperScript Preamplification System for First Strand cDNA Synthesis kit (Gibco BRL, Life Technologies) according to the manufacturers instructions. 1 nanogram of random hexamers is used to prime each reaction. Controls without the addition of SuperScriptII reverse transcriptase are also run. Both +/− RT samples are treated with RNaseH before proceeding to the PCR reaction.

e) The use of PCR to Determine the Presence of a Bacterial cDNA Species

PCR reactions are set up on ice in 0.2 ml tubes by adding the following components:
  45 microliters PCR SUPERMIX (Gibco BRL, Life Technologies).
  1 microliter 50 mM MgCl$_2$, to adjust final concentration to 2.5 mM.
  1 microliter PCR primers (optimally 18-25 basepairs designed to possess similar annealing temperatures), each primer at 10 mM initial concentration.
  2 microliters cDNA.

PCR reactions are run on a Perkin Elmer GeneAmp PCR System 9600 as follows:
  5 minutes at 95° C., then 50 cycles of 30 seconds each at 94° C., 42° C. and 72° C. followed by 3 minutes at 72° C. and then a hold temperature of 4° C.
  10 microliter aliquots are then run out on 1% 1×TBE gels stained with ethidium bromide with PCR product sizes estimated by comparison to a 100 bp DNA Ladder (Gibco BRL, Life Technologies).

RT/PCR controls may include +1-reverse transcriptase reactions, 16s rRNA primers or DNA specific primer pairs designed to produce PCR products from non-transcribed *S. aureus* WCUH29 genomic sequences.

To test the efficiency of the primer pairs they are used in DNA PCR with WCUH29 total DNA. PCR reactions are set up and run as described above using approx. 1 microgram of DNA in place of the cDNA and 35 cycles of PCR rather than 50.

Primer pairs which fail to give the predicted sized product in either DNA PCR or RT/PCR (approx 20%) are PCR failures and as such are uninformative. Of those which give the correct size product with DNA PCR three classes are distinguished in RT/PCR:

1. Genes which are not expressed in vivo reproducibly fail to give a product in RT/PCR.

2. Genes which are expressed in vivo reproducibly give the correct size product in RT/PCR and show a stronger signal in the +RT samples than in the −RT controls.

3. Genes which may be expressed in vivo give similar amounts of product in both +/−RT samples.

Table 1 sets forth certain information pertinent to cloning and identification of ORFs of the invention, such as reading frame direction (forward or reverse) on each polynucleotide in the Sequence Listing, a putative identity based on homology searches, the numbers of the first and last nucleic acid of the reading frame, and the number of codons in the ORF (including the stop codon). Using this information, expression vectors providing the selected protein are prepared and the protein is configured in an appropriate screen for the identification of anti-microbial agents.

TABLE 1

```
SEQ ID NO:1 ENCODED BY SEQ ID NO:2
ORF #;  Start  End   Direction Codon Length
1       576    1160  F 1       95 codons
ORF translation from 576-1160, direction F
Blastp and/or MPSearch Result:
Description:
2 622 38.7 262 1 FABI~ECOLI ENOYL-[ACYL-CARRIER-PR 1.40e-110
---

2) INFORMATION FOR SEQ ID NO:1:
 (i) SEQUENCE CHARACTERISTICS:
 (A) LENGTH: 194 amino acids
 (B) TYPE: amino acid
 (C) STRANDEDNESS: single
 (D) TOPOLOGY: linear
(ii) MOLECULE TYPE: protein
(xi) SEQUENCE DESCRIPTION: SEQ ID NO:1:
Met Glu Asp Leu Arg Gly Arg Phe Ser Glu Thr Ser Arg Glu Gly Phe
1               5                  10                  15

Leu Leu Ala Gln Asp Ile Ser Ser Tyr Ser Leu Thr Ile Val Ala His
                20                  25                  30

Glu Ala Lys Lys Leu Met Pro Glu Gly Gly Ser Ile Val Ala Thr Thr
            35                  40                  45

Tyr Leu Gly Gly Glu Phe Ala Val Gln Asn Tyr Asn Val Met Gly Val
        50                  55                  60

Ala Lys Ala Ser Leu Glu Ala Asn Val Lys Tyr Leu Ala Leu Asp Leu
65                  70                  75                  80

Gly Pro Asp Asn Ile Arg Val Asn Ala Ile Ser Ala Gly Pro Ile Arg
                85                  90                  95

Thr Leu Ser Ala Lys Gly Val Gly Gly Phe Asn Thr Ile Leu Lys Glu
                100                 105                 110

Ile Glu Glu Arg Ala Pro Leu Lys Arg Asn Val Asp Gln Val Glu Val
            115                 120                 125

Gly Lys Thr Ala Ala Tyr Leu Leu Ser Asp Leu Ser Ser Gly Val Thr
        130                 135                 140

Gly Glu Asn Ile His Val Asp Ser Gly Phe His Ala Ile Asn Xaa Ile
145                 150                 155                 160

Ile Gln Gln Leu Gly Phe Thr Val Tyr His Ile Leu Trp Ser Lys Ser
                165                 170                 175

Phe Xaa Gly Phe Ile Asn Asn Xaa Ala Asp Gly Lys Leu Leu Asp Ile
                180                 185                 190

Ser Thr (2) INFORMATION FOR SEQ ID NO:2:
(i) SEQUENCE CHARACTERISTICS:
(A) LENGTH: 1167 base pairs
(B) TYPE: nucleic acid
(C) STRANDEDNESS: single
(D) TOPOLOGY: linear
(ii) MOLECULE TYPE: Genomic DNA
(xi) SEQUENCE DESCRIPTION: SEQ ID NO:2:
ATATGATATT AAAATGCAGG AACGTATTTA GTACGAACGT AAAATTAATG ATTTAAAATG      60

CTAGTATGTA TATGATTTTG ATAAATAAAT GCTTTTTAAC GTAAATCAAG TTTGATACAG     120

AAAGGACTAA ATCAAAACAT TTATTCGTTG TAATAACGTT TAAATAACTT TATTAAAAAG     180
```

TABLE 1-continued

```
TCATAATAGT GTTAAAATGT ATTGACGAAT AAAAAGTTAG TTAAAACTGG GATTAGATAT    240
TCTATCCGTT AAATTAATTA TTATAAGGAG TTATCTTAAC ATGTTAAATC TTGAAAACAA    300
AACATATGTC ATCATGGGAA TCGCTAATAA GCGTAGTATT GCTTTTGGTG TCGCTAAAGT    360
TTTAAGATCA ATTAGGTGCT AAATTAGTAT TTACTTACCG TAAAGAACGT AGCCGTAAAG    420
AGCTTGAAAA ATTATTAGAA CAATTAAATC AACCAGAAGC GCACTTATAT CAAATTGATG    480
TTCAAAGCGA TGAAGAGGTT ATTAATGGTT TTGAGCAAAT TGGTAAAGAT GTTGGCAATA    540
TTGATGGTGT ATATCATTCA ATCGCATTTG CTAATATGGA AGACTTACGC GGACGCTTTT    600
CTGAAACTTC ACGTGAAGGC TTCTTGTTAG CTCAAGACAT TAGTTCTTAC TCATTAACAA    660
TTGTGGCTCA TGAAGCTAAA AAATTAATGC CAGAAGGTGG TAGCATTGTT GCAACAACAT    720
ATTTAGGTGG CGAATTCGCA GTTCAAAATT ATAATGTGAT GGGTGTTGCT AAAGCGAGCT    780
TAGAAGCAAA TGTTAAATAT TTAGCATTAG ACTTAGGTCC TGATAATATT CGCGTTAATG    840
CAATTTCAGC TGGTCCAATC CGTACATTAA GTGCAAAAGG TGTGGGTGGT TTCAATACAA    900
TTCTTAAAGA AATCGAAGAG CGTGCACCTT TAAAACGTAA CGTTGATCAA GTAGAAGTAG    960
GTAAAACAGC GGCTTACTTA TTAAGTGACT TATCAAGTGG CGTTACAGGT GAAAATATTC   1020
ATGTAGATAG CGGATTCCAC GCAATTAATA NTATCATTCA ACAGCTTGGG TTCACCGTTT   1080
ATCATATATT GTGGAGCAAA AGCTTTNTGG GTTTATTAA TAATCNGGCT GATGGAAAAT   1140
TATTGGATAT TTCAACCTGA CTTGATT                                       1167
```

---

The invention claimed is:

1. An isolated polypeptide comprising SEQ ID NO:1.

2. A composition comprising the isolated polypeptide of claim 1 and a pharmaceutically acceptable carrier.

3. The isolated polypeptide of claim 1, wherein the isolated polypeptide comprises a heterologous amino acid sequence fused to SEQ ID NO:1.

4. A composition comprising the isolated polypeptide of claim 3 and a pharmaceutically acceptable carrier.

5. The isolated polypeptide of claim 1, wherein the isolated polypeptide consists of SEQ ID NO:1.

6. A composition comprising the isolated polypeptide of claim 5 and a pharmaceutically acceptable carrier.

* * * * *